(12) United States Patent
Kronich et al.

(10) Patent No.: US 8,214,045 B2
(45) Date of Patent: Jul. 3, 2012

(54) LEAD IMPLANT SYSTEM

(75) Inventors: Christine G. Kronich, Saint Paul, MN (US); John L. Sommer, Coon Rapids, MN (US); William K. Wenger, St. Paul, MN (US); Michael D. Eggen, Lake Elmo, MN (US); Gerald Jordan Montgomery, Blaine, MN (US); Joseph A. DuPay, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 1099 days.

(21) Appl. No.: 12/112,111

(22) Filed: Apr. 30, 2008

(65) Prior Publication Data

US 2009/0276004 A1 Nov. 5, 2009

(51) Int. Cl.
*A61N 1/375* (2006.01)

(52) U.S. Cl. ........................................ 607/36
(58) Field of Classification Search ............... 607/36–37
See application file for complete search history.

(56) References Cited

U.S. PATENT DOCUMENTS

| | | | |
|---|---|---|---|
| 4,187,854 A | 2/1980 | Hepp et al. | |
| 4,830,005 A | 5/1989 | Woskow | |
| 6,269,270 B1 | 7/2001 | Boveja | |
| 6,335,492 B1 | 1/2002 | Terasaka et al. | |
| 7,103,414 B1 | 9/2006 | Poore et al. | |
| 7,289,855 B2 | 10/2007 | Nghiem et al. | |
| 7,359,752 B1 | 4/2008 | Bornzin et al. | |
| 2003/0068914 A1 | 4/2003 | Merry et al. | |
| 2004/0147822 A1 | 7/2004 | Al-Ali et al. | |
| 2004/0230267 A1 | 11/2004 | Wenger | |
| 2006/0144747 A1 | 7/2006 | Le et al. | |
| 2007/0049991 A1 | 3/2007 | Klostermann et al. | |
| 2007/0123947 A1 | 5/2007 | Wenger et al. | |
| 2007/0173900 A1 | 7/2007 | Siegel et al. | |
| 2008/0015648 A1* | 1/2008 | Libbus et al. | 607/9 |

FOREIGN PATENT DOCUMENTS

| | | |
|---|---|---|
| WO | WO 2005/082451 | 9/2005 |
| WO | 2008017059 | 2/2008 |
| WO | WO 2009/018426 | 2/2009 |

OTHER PUBLICATIONS

PCT International Search report, PCT/US09/039307, 3 pages, Jun. 22, 2009.

* cited by examiner

*Primary Examiner* — Eric D. Bertram
(74) *Attorney, Agent, or Firm* — Reed A. Duthler; Stephen W. Bauer

(57) ABSTRACT

A lead implant system includes a lead coupling device, which is configured to couple a lead during an implant procedure, in communication with a medical device and an implantable medical device, which is contained within a package that includes an electrical interface for electrical coupling with an electrical contact of the implantable medical device. The electrical interface facilitates coupling of the packaged medical device to an electrical contact of another medical device, which is located outside the package. If the electrical contact of the packaged device is mounted within a bore of the device, then the connector structure allows for passage of a sterilizing gas into the connector bore, and past the connector contact, within the bore.

13 Claims, 16 Drawing Sheets

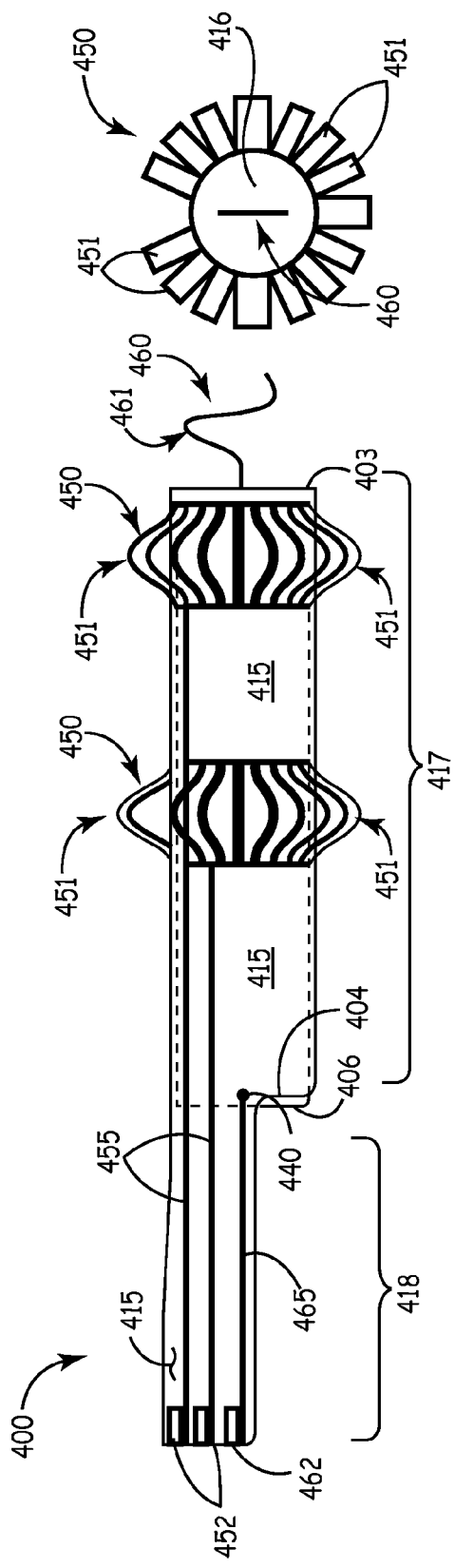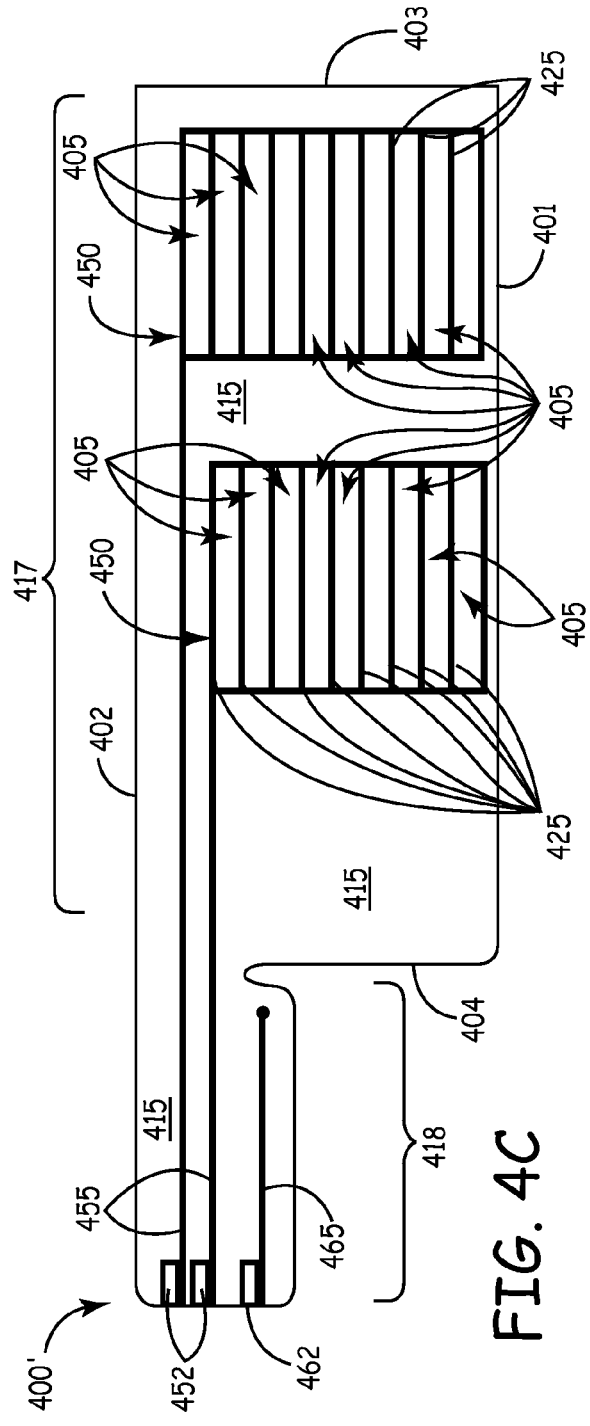

LEAD IMPLANT SYSTEM

TECHICAL FIELD

The present disclosure pertains to medical devices and more particularly to lead implant systems.

CROSS REFERENCE TO RELATED APPLICATION

Reference is made to commonly-assigned and co-pending application U.S. Ser. No. 12/112,095 filed Apr. 30, 2008, entitled "Lead-Implant Coupling Device;" U.S. Ser. No.12/112,102, filed Apr. 30, 2008, entitled "Remote Lead-Implant Coupling Device;" and U.S. Serial No. 12/112,090, filed Apr. 30, 2008, entitled "Medical Device Packaging Systems Including Electrical Interfaces," all of which are herein incorporated by reference in their entirety.

BACKGROUND

Many medical devices, particularly implantable medical devices, are provided, in sterilized packages. For medical systems that include more than one device, it is often necessary to evaluate a first device of the system prior to connecting one device to another device of the system. An exemplary system includes an implantable generator device and an implantable electrical lead, which couples the generator device to a body of a patient. The performance of various types of implantable systems ranging from cardiac and neurological stimulators to diagnostic pressure sensors relies upon an effective interface between the electrical lead of the system and a particular site within the body of the patient. To determine whether or not an effective interface can be attained as well as to verify the operability of the leads, it is prudent to evaluate the interface between the one or more leads and the patient's body, at one or more implant sites, using a generator device such as an analyzer or a programmer.

Using the generator device, rather than the sterilized implantable device, for pre-implant testing, can prevent an unnecessary removal of the implantable device from its sterile packaging, if an effective interface between the one or more leads and the body cannot be attained. However, electronic circuitry of an analyzer may differ from that of an actual implantable generator device so that, in some situations, signals measured by the analyzer can differ enough from those measured by the actual device so as to limit the usefulness of the evaluation performed with the analyzer.

BRIEF DESCRIPTION OF THE DRAWINGS

The following drawings are illustrative of particular embodiments of the present disclosure and therefore do not limit the scope of the disclosure. The drawings (not to scale) are intended for use in conjunction with the explanations in the following detailed description, wherein like numerals denote like elements.

FIGS. 4A-B are plan and end views, respectively, of an electrical interface.

FIG. 4C is a plan view of a portion of the electrical interface of FIGS. 4A-B in a pre-assembled form.

DETAILED DESCRIPTION

The following detailed description is exemplary in nature and is not intended to limit the scope, applicability, or configuration of the present disclosure in any way. Rather, the following description provides practical illustrations for implementing exemplary embodiments of the present disclosure.

Figure 1A:
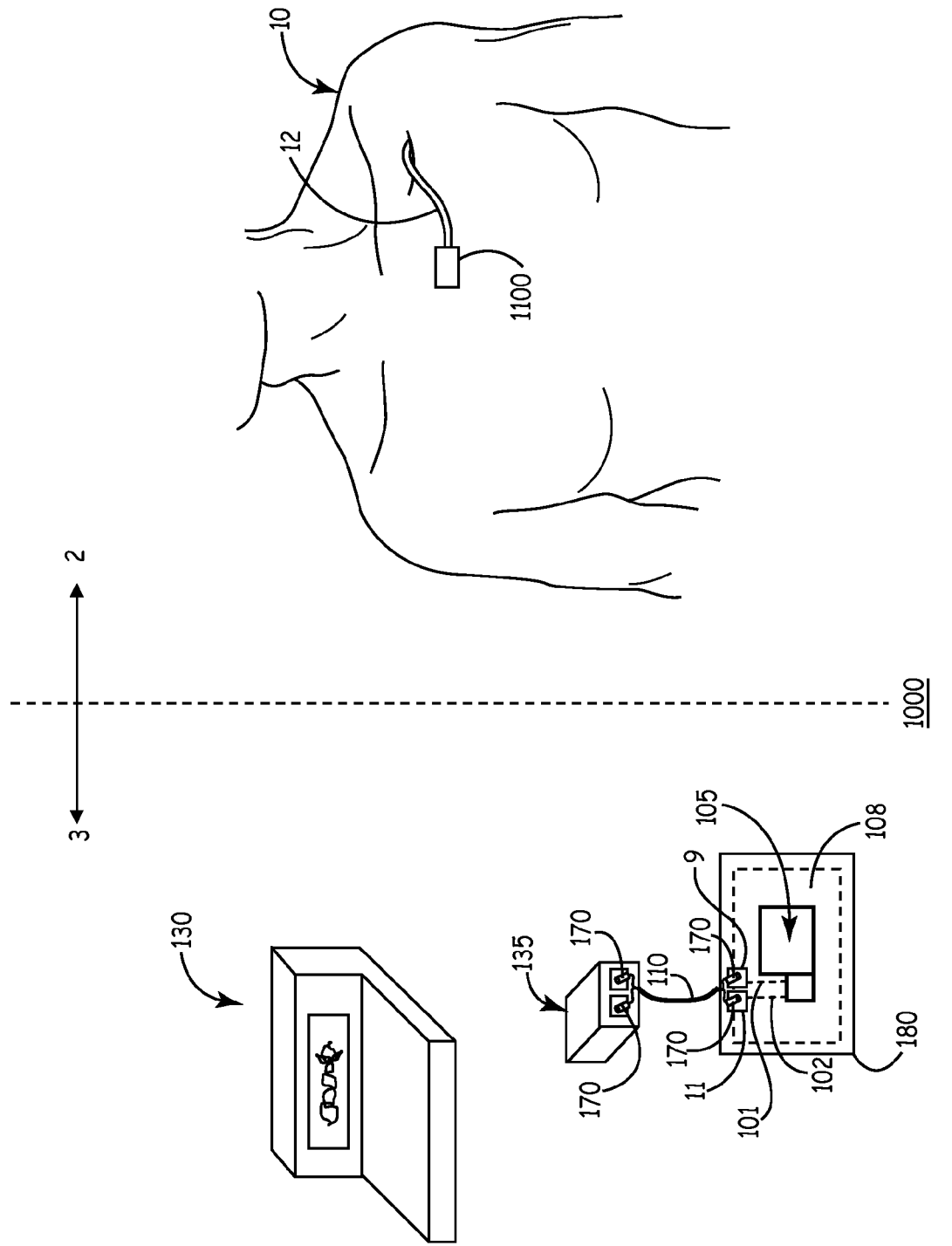
FIG. 1A is a schematic overview of a system which is coupled for pre-implant testing to an implanted electrical lead.
Figure 1B:
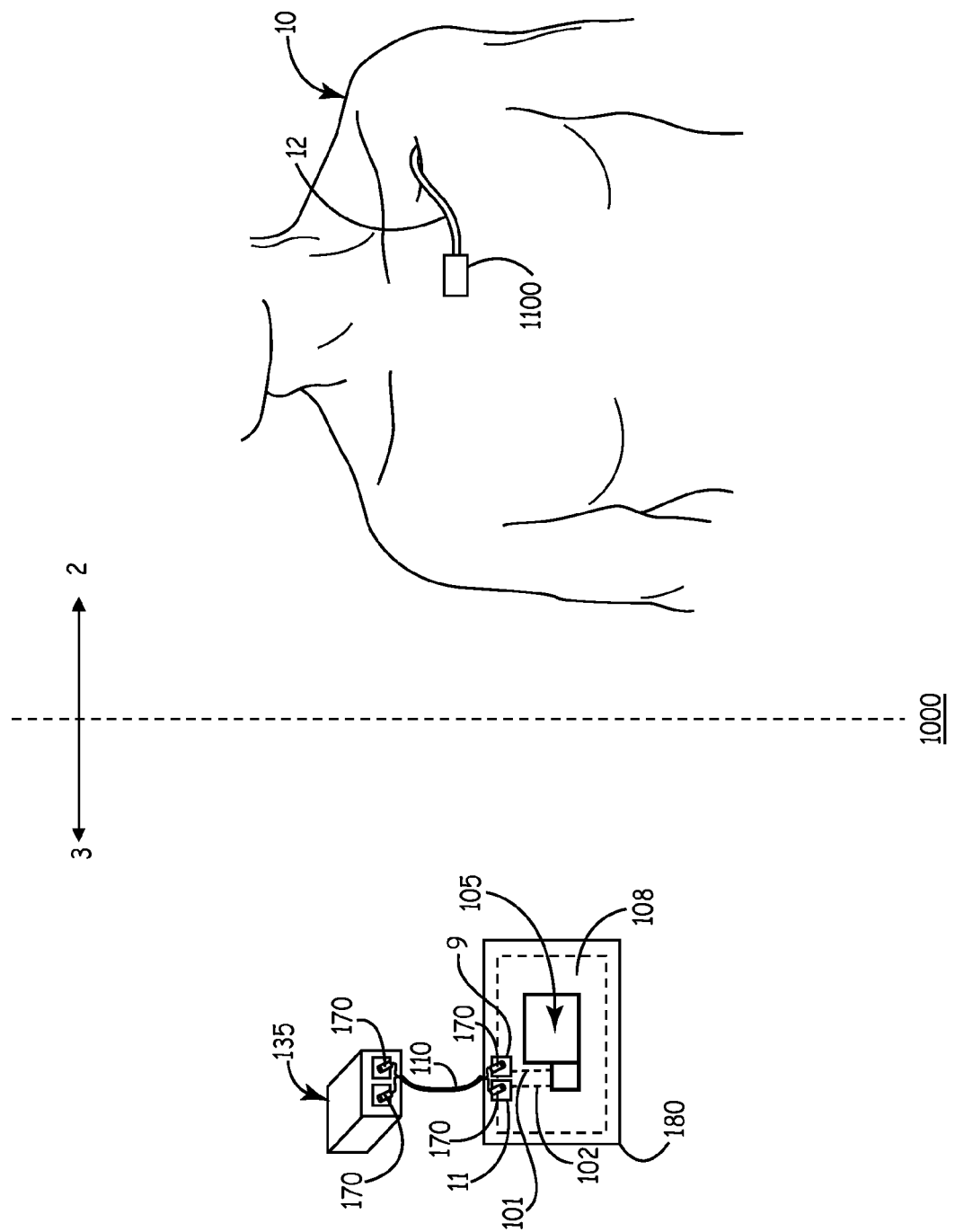
FIG. 1B is a schematic overview of an alternative system which is coupled for pre-implant testing to an implanted electrical lead.

FIGS. 1A and 1B are schematic overviews of alternative embodiments of an implanted electrical lead 12 coupled for pre-implant testing. FIGS. 1A and 1B illustrate a patient 10 (within a sterile field 2) in which the lead 12 is implanted. Adjacent to the sterile field 2 is a non-sterile field 3.

FIG. 1A depicts system 1000 which includes a programming device 130 (such as a fully functional programmer or task specific programming device such as a pacing system analyzer), a communication interface device 135, a sterile package formed by a tray 180 sealed with lid 108, an implantable generator device 105 enclosed within tray 180 (beneath lid 108), a portion of an electrical interface formed by conductive leads 101, 102 and contact surfaces 9, 11. Leads 101, 102 are shown extending from generator device 105 to contact surfaces 9, 11, which are located on an exterior side of lid 108. Connection cable 110 couples the interface device 135 to generator device 105 in tray 180 via the leads 101, 102. Each end of connection cable 110 includes a pair of alligator clips 170 for making electrical connection with contacts 9, 11 and the interface device 135.

A lead coupling device 1100 (described in more detail in FIG. 9) couples directly to the lead 12. The coupling device 1100 incorporates a wireless communication module that enables communication with the devices 130, 135 within non-sterile field 3. With the wireless communication capability, the coupling device 1100 may remain connected to the lead 12 during the entire implant procedure while permitting any desired communication with other devices in the system 1000. Interface device 135 contains a wireless communication module (not shown) that is compatible with that of coupling device 1100.

Interface device 135 functions as a signal "repeater" by receiving signals, such as data or commands, transmitted by the generator device 105 or the programmer 130 and relaying them to the coupling device 1100. Conversely signals transmitted by the coupling device 1100 are relayed to the generator device 105 or the programmer 130. In one embodiment, a physical wired connection (not shown) couples the interface device 135 and the programmer 130 for communication between the devices. In another embodiment, the programmer 130 and the interface device 135 communicate wirelessly.

FIG. 1B shows an alternate embodiment of system 1000 which includes interface device 135, generator device 105 contained within the sterile package formed by tray 180 sealed with lid 108, and lead coupling device 1100 coupled directly to lead 12. The electrical interface formed by conductive leads 101, 102 and contact surfaces 9, 11 mechanically and electrically couple generator device 105 to interface device 135 through connection cable 110. Interface device 135 receives signals transmitted by the coupling device 1100 and relays them to the generator device 105. Similarly, interface device 135 transmits signals sent by the generator device 105 to coupling device 1100.

Figure 2:
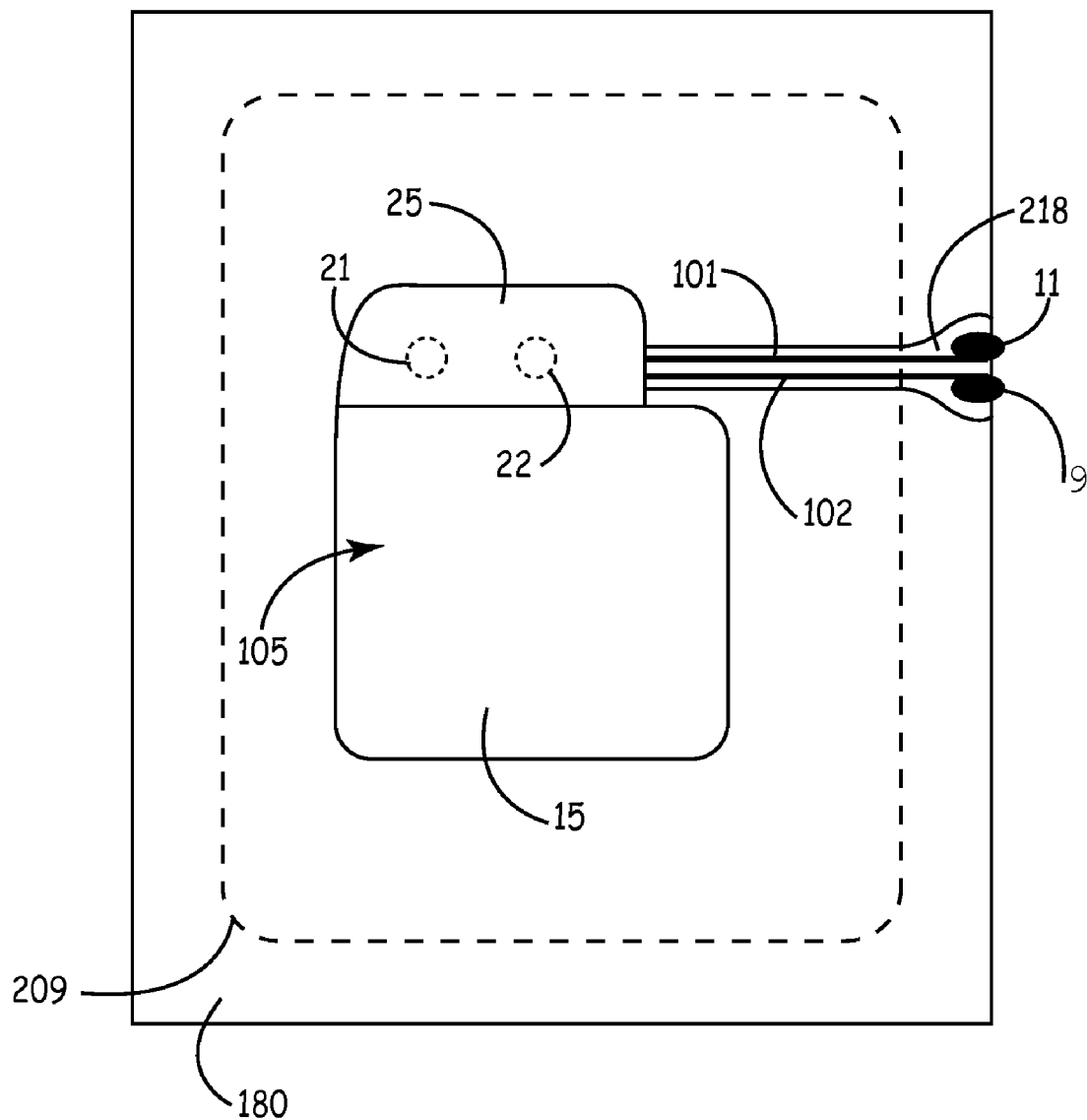
FIG. 2 is an enlarged plan view of a portion of the system shown in FIG. 1A.

FIG. 2 illustrates tray 180 with lid 108 removed to show the substrate 218 of the electrical interface, which crosses through a seal zone 209 (shown with dashed lines) between lid 108 and tray 180, and along which conductive leads 101, 102 extend. Contact surfaces 9, 11 are shown terminating conductive leads 101, 102, on substrate 218 at an edge of tray 180.

Substrate 218 may be a flexible insulative substrate on which leads 101, 102 and contact surfaces 9, 11. Although not explicitly shown, it should be appreciated that substrate 218 may extend beneath leads 101, 102 and contact surfaces 9, 11, on a side of tray 180 may extend over leads 101, 102 and contact surfaces 9, 11 on an opposite side thereof, adjacent to lid 108. Such an insulative layer may promote better adhesion between lid 108 and the portion of the electrical interface that extends through seal zone 209.

It will be appreciated that the electrical interface electrically couples electrical contacts 21, 22 of generator device 105 via conductive leads 101, 102, to contact surfaces 9, 11, as will be described in greater detail below, so that cable 110 electrically couples lead 12 to generator device 105 without having to remove generator device 105 from the package, or to peel back lid 108 from tray 180. Alternative embodiments to the portion of the electrical interface, which is shown in FIG. 2, will be described in greater detail below, in conjunction with FIGS. 7A-D and 8A-C.

Figure 3B:
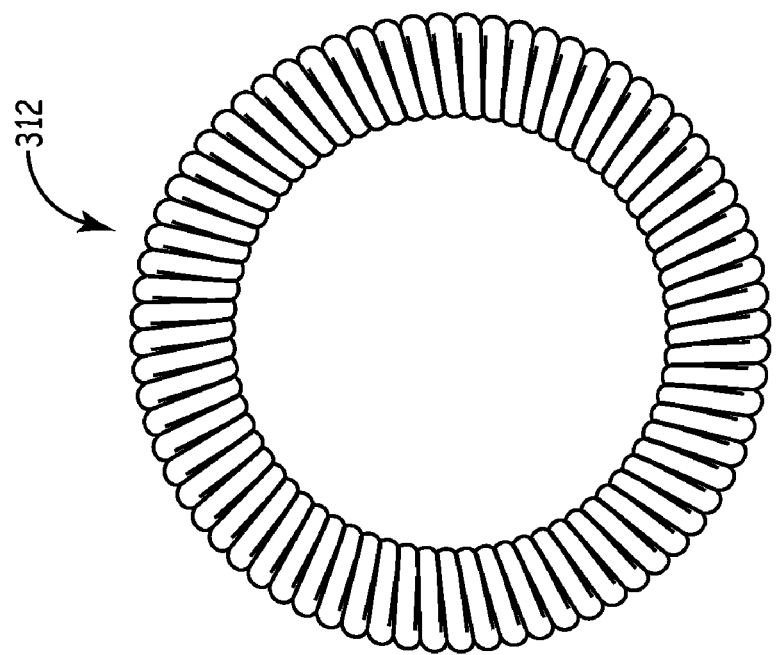
FIG. 3B is a plan view of an alternative electrical contact, which may be incorporated with a connector bore of an implantable generator device.
Figure 3A:
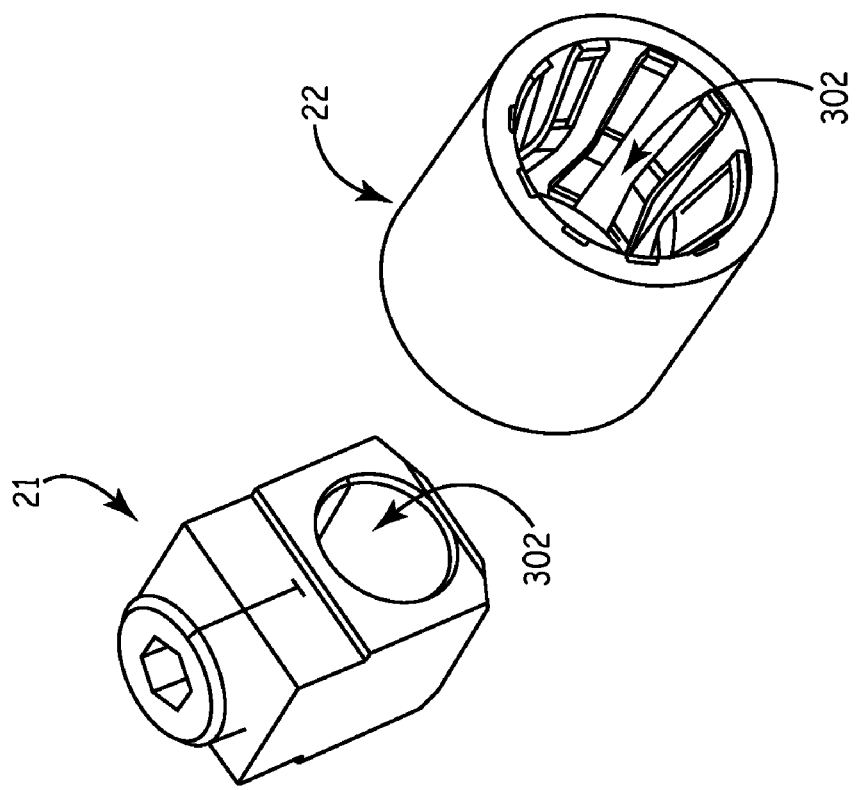
FIG. 3A is a perspective view of two types of electrical contacts that may be incorporated within a single connector bore of an implantable generator device.

FIG. 2 further illustrates generator device 105 including a can, or housing 15 which encloses a battery and electronic circuitry, and a connector module 25, having a bore (not shown) in which connector contacts 21, 22 are mounted for electrically coupling with a lead connector, according to methods known to those skilled in the art. Examples of connector contacts 21, 22 are illustrated in FIG. 3A, as they may be arranged within the bore of module 25, longitudinally spaced apart from one another and having their bores 302 extending approximately coaxially with the bore of module 25. An alternative connector contact 312, which may be substituted for either of contacts 21, 22 is shown in FIG. 3B. Contact 21 is shown as a set screw type contact, contact 22 as a multi-beam type contact, and contact 312 as a garter spring-type contact. With reference back to FIG. 2, it may be appreciated that each of the other contact surfaces of the electrical interface, which are not shown, are positioned to make electrical contact with contacts 21, 22, inside the bore of module. According to embodiments of the present disclosure, a connector structure of the electrical interface, which supports these other contact surfaces, within the bore of generator device 105, is constructed so as to allow a passage of a sterilizing gas into the bore of generator device 105 in order to ensure complete sterility of generator device 105. Various embodiments of connector structures for electrical interfaces will now be described in conjunction with FIGS. 4-6

FIGS. 4A-B are plan and end views, respectively, of an electrical interface 400. FIG. 4A illustrates a relatively thin and flexible substrate 415 forming a portion of interface 400 and including a tubular first part 417 and a relatively flat second part 418. FIGS. 4A-B illustrate tubular first part 417 being wrapped about a pin member 416 of interface 400 and including a pair of segments, which are each deformed into a plurality of protruding curved beams 450. With reference to FIG. 4C, which illustrates first portion 417 in a relatively flat, pre-assembled form, each of the plurality of beams 450 is separated by a cut-out portion, or slit 405 in substrate 415, and bears a conductive trace 425 with each conductive trace 425 extending to a corresponding conductive lead 455. Each lead 455 extends along first portion 417 of substrate 415 to second portion 418 of substrate 415 to couple traces 425 to corresponding contact surfaces 452, which are mounted to second portion 418. Although each of the plurality of beams 450 are shown bearing a conductive trace 425, it should be noted that embodiments of the present disclosure are not so limited and any number of beams of each plurality 450 may bear a trace 425. Microflex, or miniature-scale micro-circuit technology may be employed to apply the traces to, and form the slits in substrate 415.

According to the illustrated embodiment, opposing edges 401, 402 of first portion 417 of substrate 415 are coupled at the seams around pin member 416, and then an end 403 of substrate 415 may be pushed toward an opposing end 404 in order to deform, or buckle, the beams of each plurality of beams 450 so that an apex of each curved beam, that bears conductive trace 425, forms one of contact surfaces 451, as shown in FIGS. 4A-B. The maximum dimension of an outer perimeter of each plurality of protruding beams 450 is tailored to be sufficiently large so that contact surfaces 451 mate within a bore of a particular electrical contact, with sufficient rigidity to maintain a stable electrical contact between each contact surface 451 and the corresponding electrical contact, while maintaining a position of each apex in proximity to a sidewall of the connector bore so as to provide a space beneath each beam. The space provided by this connector structure allows for passage of a sterilizing gas within a connector bore and past the electrical contacts mounted therein of a packaged device.

FIGS. 4A-B further illustrate electrical interface 400 including another contact surface 461, which is formed at an apex of a relatively rigid, curved and protruding beam 460, which extends proximally from pin member 416 and may be formed integrally therewith, according to some embodiments. In one embodiment, contact surface 461 is electrically coupled to another contact surface 462, which is mounted alongside contact surface 452 on second part 418 of substrate 415, via pin member 416 and another conductive lead 465. Pin member 416 is formed from any conductive material such as stainless steel. FIG. 4A illustrates a distal end 404 of pin member 416 coupled to conductive lead 465 at a connective interface 440. The pair of plurality of beams 450 are shown longitudinally spaced apart from one another, and from beam 460, so as to each be located for electrical coupling with a corresponding electrical contact, for example, any of contacts 21, 22, 312 (FIGS. 3A-B), within a bore of a connector module of a generator device, when electrical interface 400 is assembled together with the device inside a package for sterilization. (Although the previously depicted generator device 105 was described as including only a pair of electrical contacts 21, 22 mounted within the bore of module 25, it should be appreciated that such a device may include a connector bore that includes three or more electrical contacts mounted therein for mating with each of the contact surfaces 451, 461 of electrical interface 400.) According to alternate embodiments, curved beam 460 may only function to provide positional stability within a connector bore so that the apex of beam 460 interfaces non-conductively with a sidewall within the connector bore, in which case beam 460 and pin member 416 may be formed from a non-conductive material and conductive lead 465, along with contact surface 462, are absent from interface 400.

With yet further reference to FIG. 4A, in conjunction with FIG. 2, it may be appreciated that second portion 418 of substrate 415 is dimensioned to extend through a package, which contains the device to which contact surfaces 451, 461 are electrically coupled, from within the package, so that contact surfaces 452, 462 may be positioned on an exterior side of the package, similar to contact surfaces 9, 11. According to some alternate embodiments, an entirety of electrical interface 400 is contained within the package such that contact surfaces 452, 462 are located within the package for coupling with an auxiliary portion of the electrical interface, which auxiliary portion may be formed on a side wall of the package for direct coupling with contact surfaces 452, 462, for example, similar to the embodiment described below in conjunction with FIG. 7A. Alternatively, the auxiliary portion further includes a connective interface such as is described in greater detail below, in conjunction with FIG. 7D.

Figure 5:
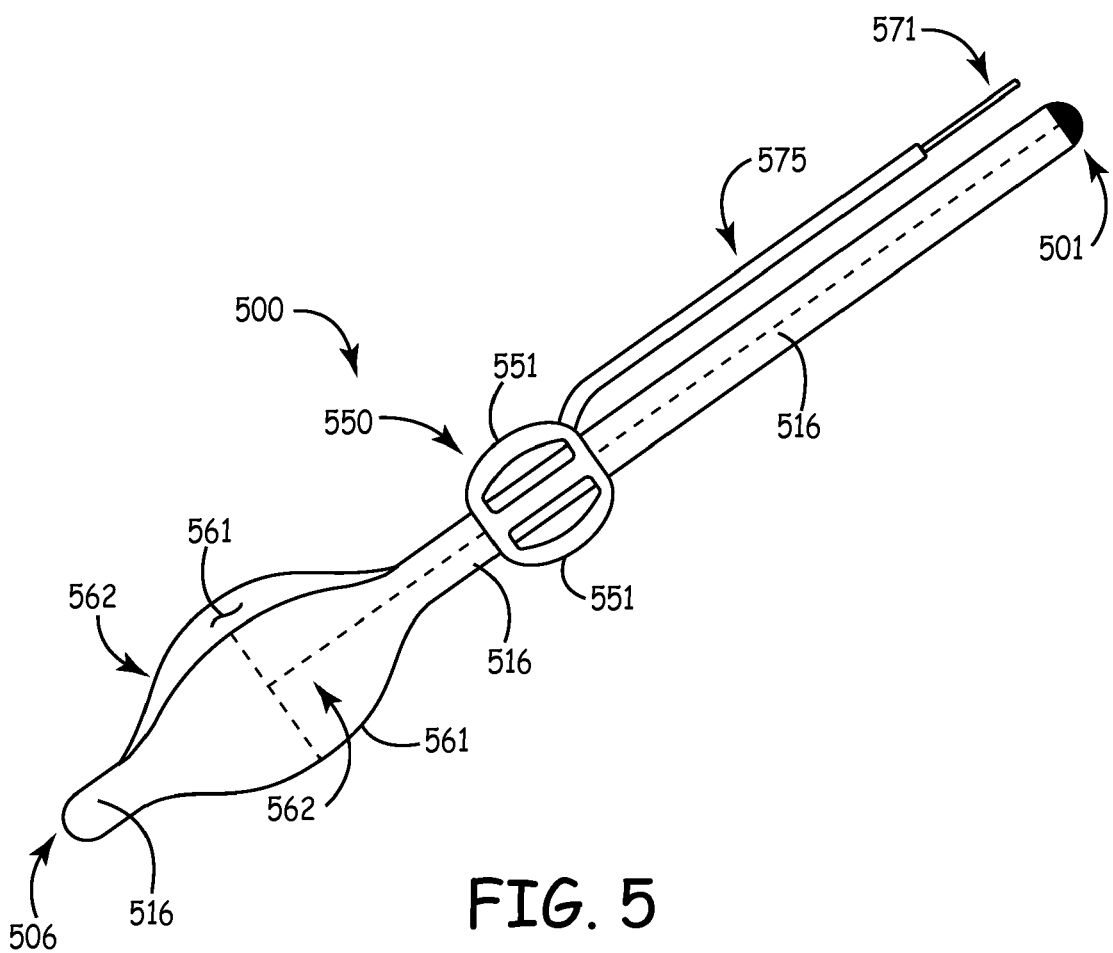
FIG. 5 is a perspective view of a connector portion for an electrical interface.

FIG. 5 is a perspective view of a connector portion 500 for an electrical interface. In the illustrated embodiment, connector portion 500 includes a pin member 516 and a plurality of protruding beams 550 arranged about pin member 516. Pin member 516 includes a pair of approximately flattened sides 562, which oppose one another and extend between a pair of arching sides, which each include a contact surface 561 that is electrically coupled to a distal end 501 of pin member 516, which distal end 501 forms a contact surface for coupling to a remainder of the electrical interface, for example, as will be described below, in conjunction with FIGS. 7A-C. FIG. 5 further illustrates additional contact surfaces 551, located at an apex of a corresponding beam of the plurality of beams 550. An insulated conductor 575 is coupled to the contact surfaces 551 and extends to a distal end 571. The distal end 571 has a contact surface for coupling to a remainder of the electrical interface, for example, as will also be described below, in conjunction with FIGS. 7A-C. With reference back to FIG. 4A, it may be appreciated that the connector structure associated with contact surfaces 551 is similar in form to that associated with contact surfaces 451.

In one embodiment, a bulk of pin member 516 may be formed from a conductive material so that contact surfaces 561 are integral with the bulk of pin member 516 and an insulating layer, for example, formed by a fluoropolymer or polyimide coating formed on pin member 516, may be necessary to isolate beams 550 from pin member 516. Alternatively, the bulk of pin member 516 may be formed from an insulative material, for example, Polyetheretherketone (PEEK), so that conductive surfaces 561 are attached to arching sides and coupled to a conductor, shown with a dashed line, which is embedded within the bulk of pin member 516 and extends from contact surfaces 561 to distal end 501 in order to couple contact surfaces 561 to distal end 501.

Figure 6:
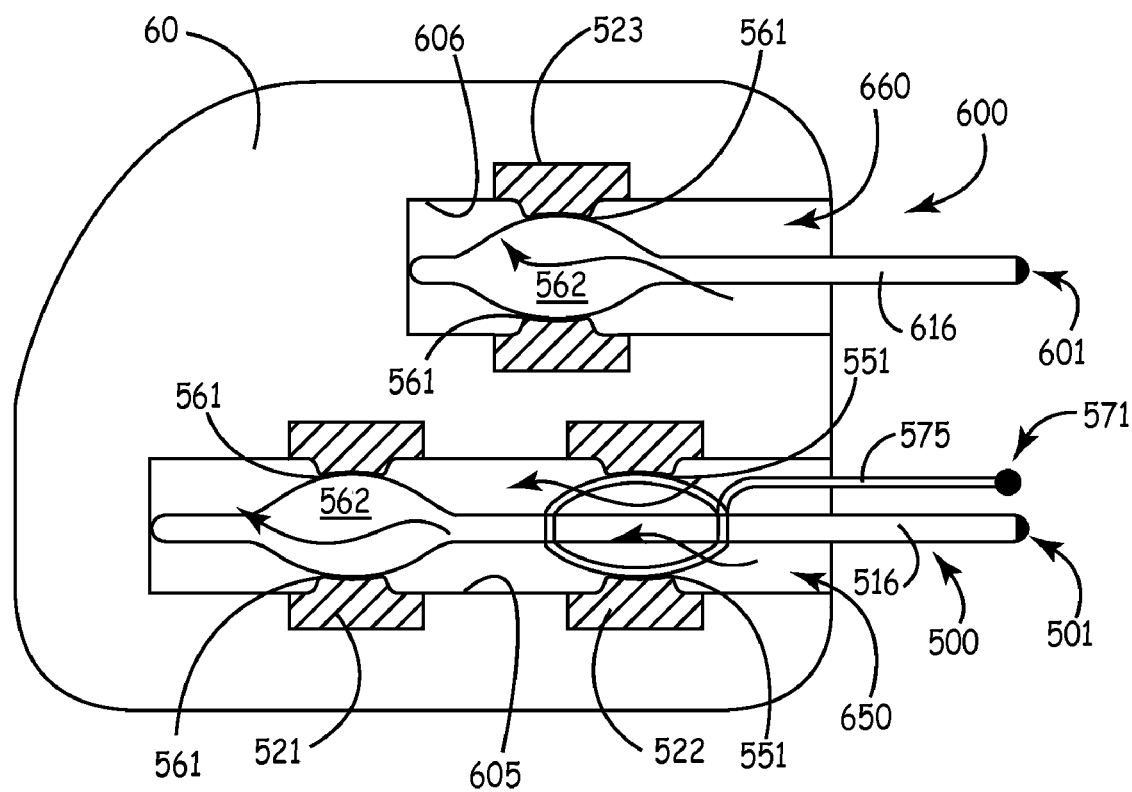
FIG. 6 is a schematic section view through a connector module of an implantable generator device to which a pair of connector portions, according to some embodiments of the present disclosure, are electrically coupled.

Turning now to FIG. 6, which is a schematic section view through a pair of connector bores 650, 660 of a connector module 60 of an implantable generator device 705 (FIG. 7A), an electrical coupling of connector portion 500 and another connector portion 600, within bores 650 and 660, respectively, according to some embodiments of the present disclosure, will be described. FIG. 6 illustrates connector bore 650 including two spaced apart electrical contacts 521, 522 mounted within a sidewall 605 thereof, and connector bore 660 including a single electrical contact 523 mounted within a sidewall 606 thereof. Contacts 521, 522, 523 may be any of the contacts 21, 22, 312 depicted in FIGS. 3A-B. It should be noted that connector portion 600 includes a pin member 616, which is formed into a connector structure supporting contact surfaces 561, for connector portion 500; a bulk of pin member 616 is preferably conductive and includes a distal end 601 serving as another contact for electrical coupling to a remaining portion of the electrical interface. According to the illustrated embodiment, connector portion 500 is inserted into bore 650, such that contact surfaces 561 and 551 are electrically coupled to electrical contact 521 and 522, respectively; and, connector portion 600 is inserted into bore 660, such that contact surfaces 561 are electrically coupled to electrical contact 523. Arrows shown within each bore 650, 660 schematically depict a flow of sterilizing gas, which is allowed passage past each of electrical contacts 521, 522, 523, by the spaces in the corresponding connector structures, between each beam of plurality of beams 550, and spaces between approximately flattened surfaces 562.

Figure 7A:
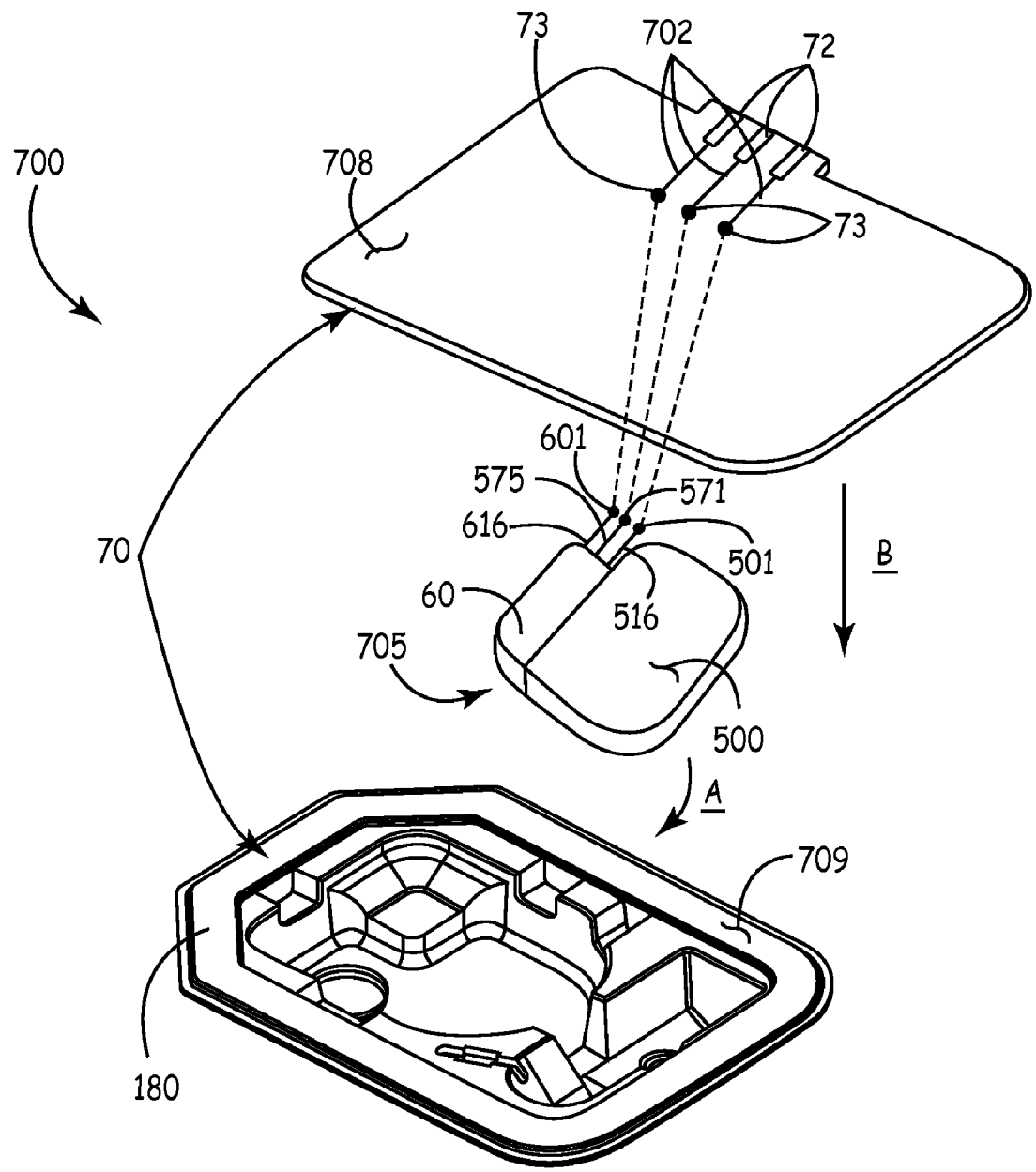
FIG. 7A is an exploded perspective view of a system including an electrical interface.

According to some embodiments of the present disclosure, distal ends 501, 571, 601 of connector portions 500, 600 are connected to the remaining portion of the electrical interface to complete an electrical coupling between contact surfaces 551, 561 and corresponding contact surfaces, which are located on an exterior surface of a package 70 containing generator device 705 (FIG. 7A). According to some embodiments, for example, as depicted in FIG. 7A, distal conductive leads 702, internal contact surfaces 73 and external contact surfaces 72 form the remaining portion of the electrical interface. Leads 702, which are formed along a side wall or lid 708 of a package 70, each couple a corresponding pair of contact surfaces 72, 73 to one another. Each contact surface 73 is positioned to directly couple a corresponding end 501, 571, 601 to a corresponding external contact surface 72 mounted on lid 708, near a perimeter of tray 180.

FIG. 7A is an exploded perspective view of a system 700 including package 70, device 705 and the electrical interface formed by connector portions 500, 600 (FIG. 6) and lid 708 of package 70. According to the illustrated embodiment, tray 180 includes a cavity into which device 705 is placed, per arrow A; the cavity of tray 180 has a profile to hold device 705 in a position so that ends 501, 571, 602 are each located, and maintained in that location, for mating with the corresponding contact surface 73, when lid 708 has been placed over device 705, in tray 180, per arrow B, and has been sealed to tray 180 along a seal zone 709. With reference back to FIG.

1A, it may be appreciated that a connector of a connection cable that is coupled to interface device 135 may be coupled to each contact 72 of system 700 in order to electrically couple device 705 to the coupling device 1100 for electrical testing, without having to remove device 705 from package 70.

Figure 7B:
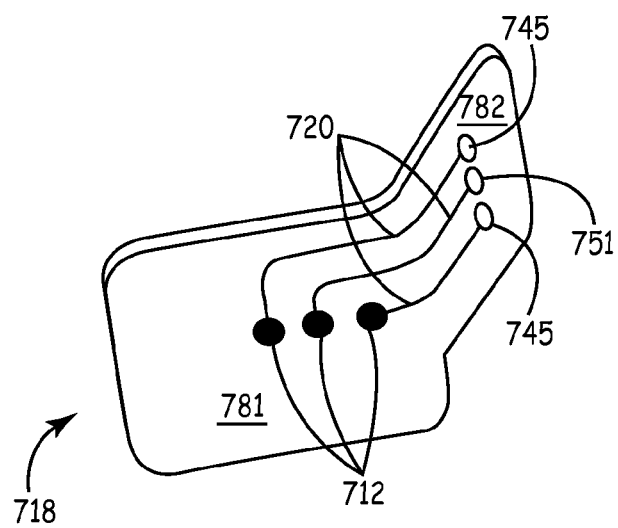
FIG. 7B is a perspective view of a portion of an electrical interface.

FIG. 7B is a perspective view of connective interface 718 which may be included in the electrical interface shown in FIG. 7A, according to some alternate embodiments. FIG. 7B illustrates interface 718 including a relatively thin and flexible substrate divided into a first segment 781 and a second segment 782, wherein second segment 782 is bent away from first segment 781. Three contact surfaces 712 are shown being formed on first segment 781, as well as corresponding conductive leads 720 extending therefrom, along first segment 781 to second segment 782, and along second segment 782. FIG. 7B further illustrates two conductive apertures 745 formed in second segment 782, wherein each one is coupled to a corresponding conductive lead 720, and terminal end 751 of another of the conductive leads 720 located on second segment 782. According to the illustrated embodiment, apertures 745 and terminal end 751 provide conductive surfaces which are oriented for electrical coupling with distal ends 501, 571, 601 of connector portions 500, 600, for example as illustrated in FIG. 7C; and contact surfaces 712 are disposed on first segment 781, which is oriented to be 'sandwiched' between a surface 715 of device 705 and lid 708 in order to provide for electrical coupling with contact surfaces 73, which are formed on lid 708 (FIG. 7A).

Figure 7C:
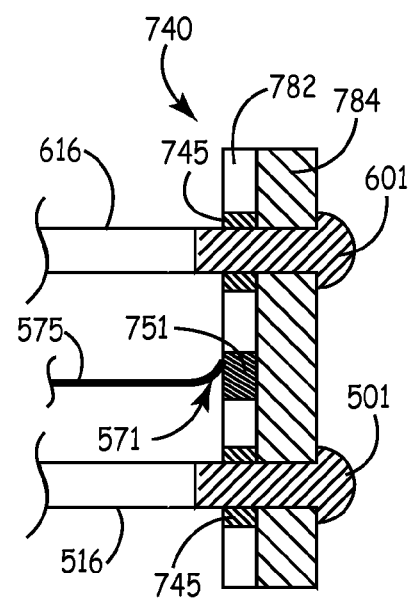
FIG. 7C is an enlarged section view through a segment of the portion of the electrical interface shown in FIG. 7B, in combination with the connector portions of FIG. 6.

FIG. 7C is an enlarged section view through second segment 782 of connective interface 718, in combination with connector portions 500, 600 (FIG. 6), which are coupled thereto. FIG. 7C illustrates the contact surfaces of apertures 745, each being formed by a conductive lining and distal ends 501, 601 of each of pin members 516, 616 extending through a corresponding aperture 745, and through an optional backing member 784 (serving as a stiffener), and being deformed to have a mushroom-like cap in order to secure the contact surfaces of ends 501, 601 within conductive apertures 745. FIG. 7C further illustrates the contact surface of distal end 571 of conductor 575 (part of connector portion 500) being coupled to terminal end 751. With reference back to FIG. 6, it can be seen that connector portions 500, 600 extend from respective bores 650, 660, so that respective distal ends 501, 571 and 601 are spaced away from each bore entry; thus second segment 782 of connective interface 718, as illustrated in FIG. 7C, will not block sterilizing gas from entering into bores 650, 660.

Figure 7D:
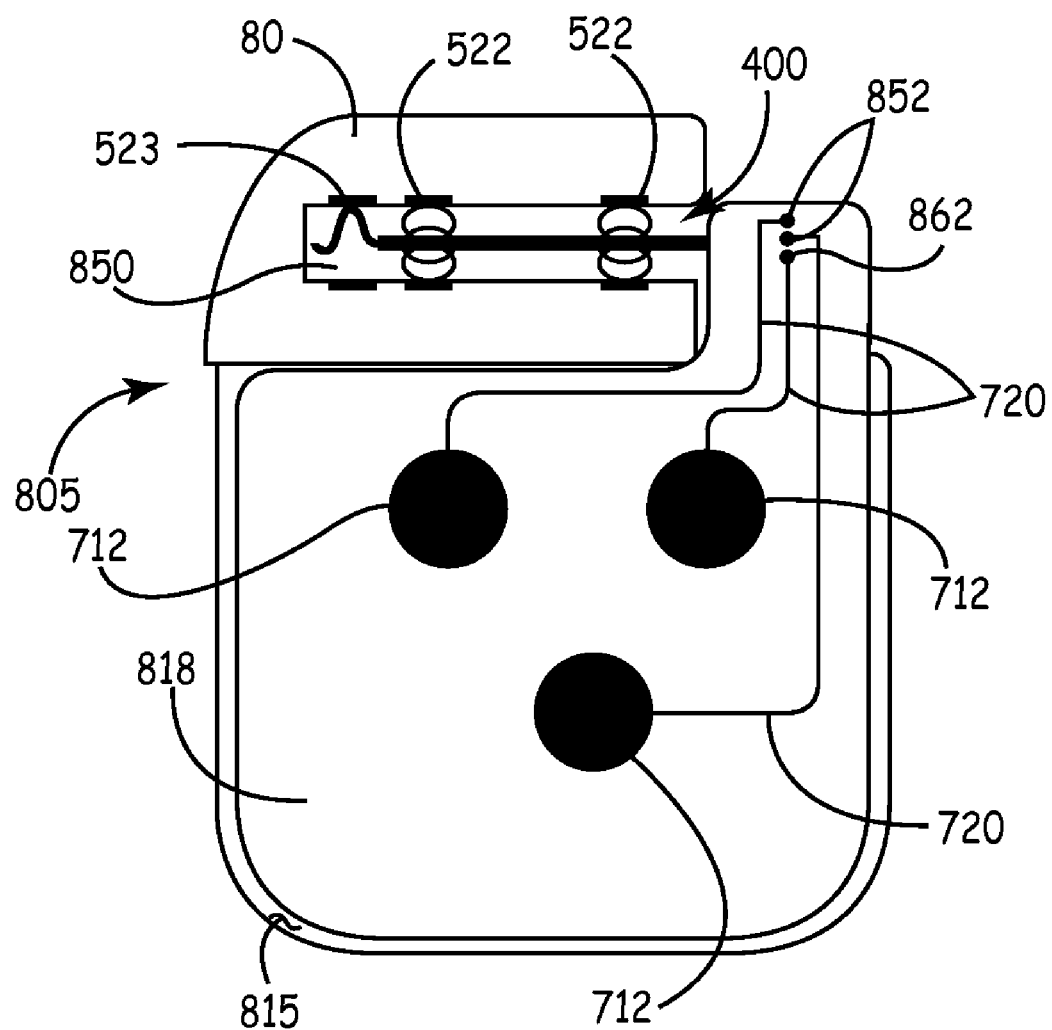
FIG. 7D is a plan view of a portion of an electrical interface.

FIG. 7D is a plan view of a portion of an electrical interface, according to some alternate embodiments, which includes a connective interface 818 coupled to electrical interface 400, which interface 400 was previously described in conjunction with FIGS. 4A-C. FIG. 7D illustrates interface 400 electrically coupled to a device 805 (schematically shown via a cut-away section through a connector module 80 of device 805), and connective interface 818 including contact surfaces 852 and 862, which are electrically coupled to contact surfaces 452 and 462, respectively, of interface 400 (see FIG. 4A). According to the illustrated embodiment, like connective interface 718, conductive leads 720 of interface 818 couple each of contact surfaces 852, 862 to a corresponding contact surface 712, and contact surfaces 712 are positioned to be 'sandwiched' between a surface 815 of device 805 and lid 708 of package 70 in order to mate with contact surfaces 73, which are formed on lid 708 (FIG. 7A).

Figure 8A:
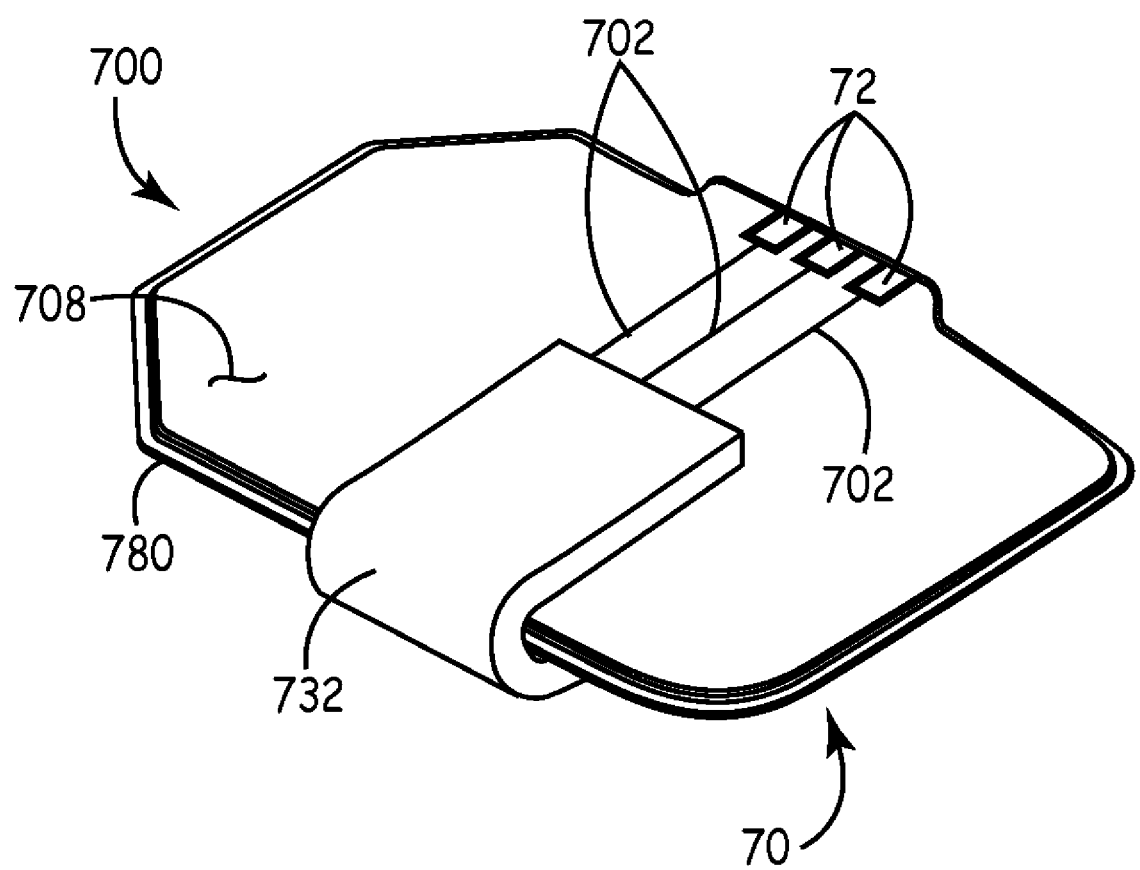
FIG. 8A is a perspective view of a system, according to an additional embodiment.

FIG. 8A is a perspective view of system 700 including a holding accessory 732, according to yet further embodiments of the present disclosure. FIG. 8A illustrates accessory 732 clamped onto package 70, over contact surfaces 73 (FIG. 7A), so as to apply pressure to maintain a stable electrical coupling between each contact surface 73 and the corresponding contact surface within package 70. The corresponding contact surfaces may be ends 501, 571, 601 of connector portions (FIG. 7A), or contact surfaces 712 of either of connective interfaces 718, 818 (FIGS. 7B-D).

Figure 8B:
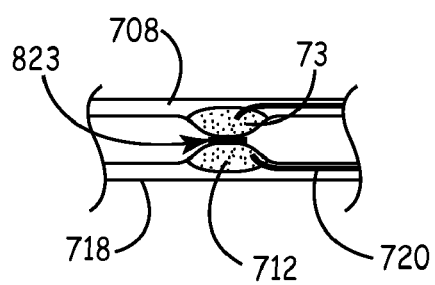
FIGS. 8B-C are section views of alternate embodiments of a coupling interface for some electrical interfaces of the present disclosure.
Figure 8C:
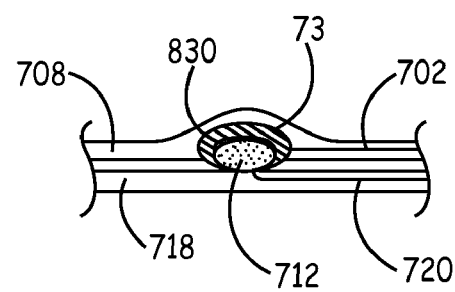

FIGS. 8B-C are section views of alternate embodiments of a coupling interface between one of contact surfaces 73 and one of contact surfaces 712, each of which may serve to maintain a stable electrical coupling therebetween, for example, without a need for accessory 732 of FIG. 8A. FIG. 8B illustrates a conductive adhesive 823 located between contact surface 73 and contact surface 712 to adhere surfaces 73, 712 to one another. Conductive adhesive 823 is preferably formulated to have a relatively weak peel strength so that when lid 708 is peeled back from tray 180, the surfaces 73, 712 may be easily separated from one another without dislodging device 705, 805 from tray 180, prior to taking device 705, 805 out from tray 180 and into the sterile field. FIG. 8C illustrates contact surface 73 formed in a recessed portion 830 of lid 708, and contact surface 712, which protrudes from a surrounding surface of first segment 781 of interface 718 to interlock with surface 73 within recess 830. Such an interlock may also be easily separated when lid 708 is peeled back.

Figure 9:
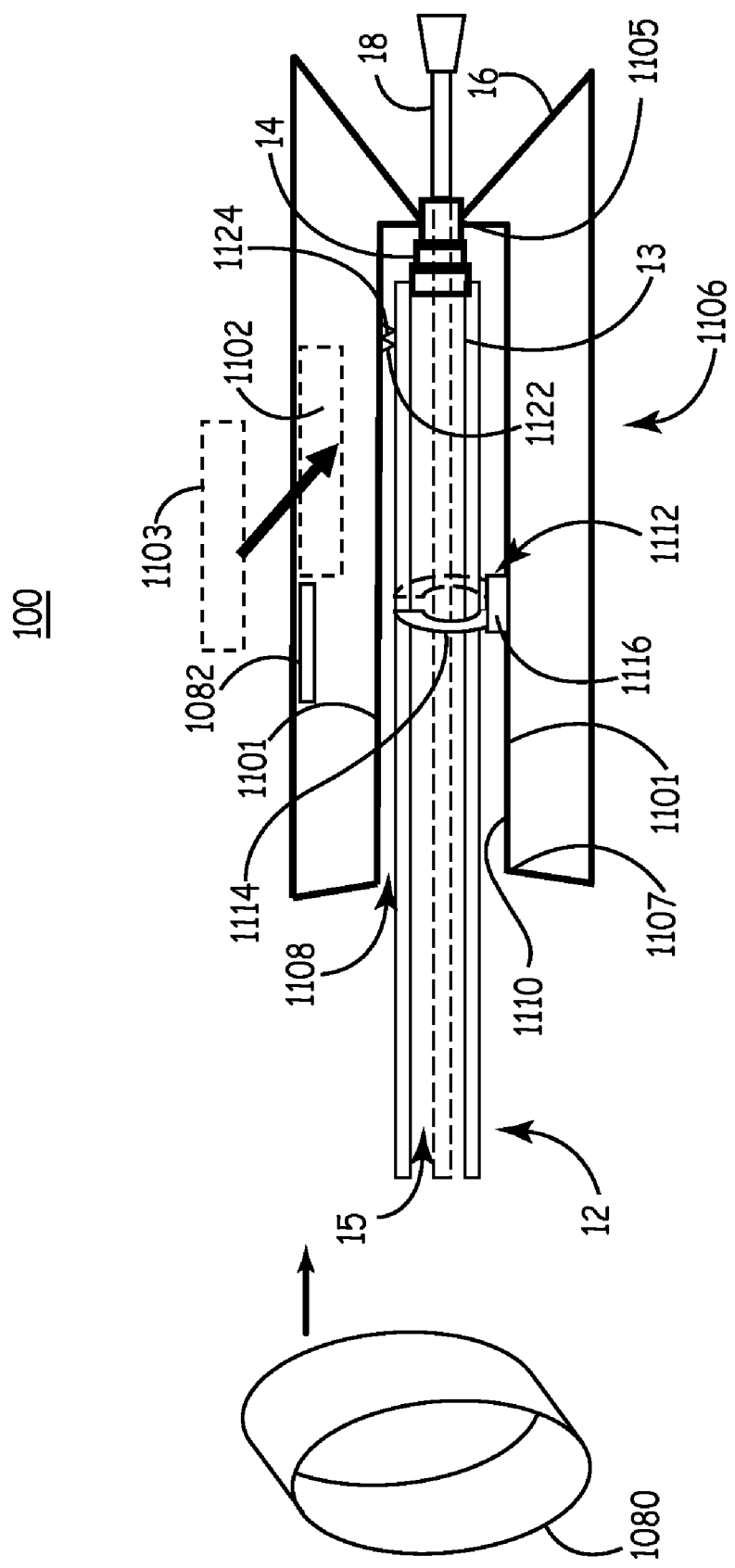
FIG. 9 is a side sectional view of the coupling device coupled to an electrical lead.

FIG. 9 is a side sectional view of a coupling device 1100 coupled to lead 12. The lead 12 includes a connector pin 14 at a proximal end 13 of lead 12 and an opening (not shown) that extends to lumen 15. It may be noted that the lead 12 is merely exemplary, and many other lead configurations may be employed with the present disclosure. The coupling device 1100 includes a housing 1106 with electronic components (FIG. 11) disposed within the housing 1106. The housing 1106 can be fabricated from any suitable material, including plastic or metal, that can be properly sterilized for use in a surgical field. In an exemplary embodiment, housing 1106 is formed from a molding fabrication process. The molding process includes mounting the electronic components on an inner layer 1101 of a plastic material and subsequently coating the electronics through an overmold process. Alternatively, the housing 1106 may be formed with an electronics component chamber 1102, having a cover 1103 that provides access to the electronic components.

The outer surface of housing 1106 may include a gripping or textured surface (e.g., ridges) to facilitate handling of the coupling device 1100. In alternate embodiments, a sleeve 1080 may be provided for placement over the housing 1106 to facilitate gripping.

A lead channel 1108 is disposed within the housing 1106 to receive the proximal portion 13 of lead 12. The lead channel 1108 extends from a distal opening 1107 to a proximal opening 1105 and guides the lead 12 toward the proximal end of the coupling device 1100. In one embodiment, the size of the proximal opening 1105 and distal opening 1107 is selected to be larger than the diameter of lead 12.

In some embodiments, a guide tool 18, such as a stylet or a guidewire, designed to facilitate maneuvering of the lead 12 is inserted through the lumen 15. The tool 18 provides additional rigidity to lead 12 and facilitates navigation. However, due to the small diameter of certain of the lead 12 configurations, the lumen is similarly small. To facilitate the insertion of the tool 18 into the lumen 15, the distal opening 1107 is provided with a tapered portion 16. The tapered portion 16 provides an enlarged opening that facilitates the insertion of tool 18 into the lumen 15.

An optional lead engagement mechanism 1112 may be provided to facilitate gripping of the lead 12. Functionally, the engagement mechanism acts to grip the body of lead 12 so that torque can be applied to the lead 12 by rotating the coupling device 1100. Alternatively, the lead channel 1108 alone, or in combination with the engagement mechanism 1112 can be configured to grip the lead 12 through a frictional fit. As used herein, gripping includes but is not limited to clamping, squeezing, locking, sliding, compressing, screwing, twisting, snapping, interlocking, or otherwise causing appropriate engagement between the lead 12 and the coupling device 1100.

In the embodiment illustrated in FIG. 9, engagement mechanism 1112 is a resilient member having a C-shaped clamp 1114 affixed to a base 1116 and medially disposed within the lead channel 1108. The clamp 1114 is resilient or spring biased so that insertion of the lead 12 causes the clamp 1114 to expand and generate an interference fit. Alternatively, other shapes, prong or clamp configurations could be employed. The C-shaped clamp 1114 or equivalent interference fit arrangements do not require additional actions to be taken by the implanting physician beyond insertion of the lead 12 into the coupling device 1100. Alternative active clamping mechanisms may be used that provide additional gripping force, but do require additional steps in their use along with additional components. The particular configuration selected will depend upon the leads being implanted and the active fixation requirements of those leads.

In general, the force required to insert the lead 12 into the lead channel 1108 will depend upon the mechanism employed to grip the lead 12. For example, the resilient clamp 1114 will require sufficient force to overcome the spring tension or resiliency of the clamp 1114. A lead channel 1108 providing a frictional lock will require sufficient force to overcome the frictional forces. With an active external clamping mechanism, seating the lead 12 would require little applied force, as the gripping force is selectively applied after insertion. Nonetheless, it is desirable for the lead 12 to be insertable into the lead channel 1108 with as minimal force as possible. By way of example, but not limitation, the mechanism employed may be configured such that only a minimal force ranging from 1.5 lbs to 2.5 lbs would be required to insert the lead 12 into the lead channel 1108.

Figure 10:
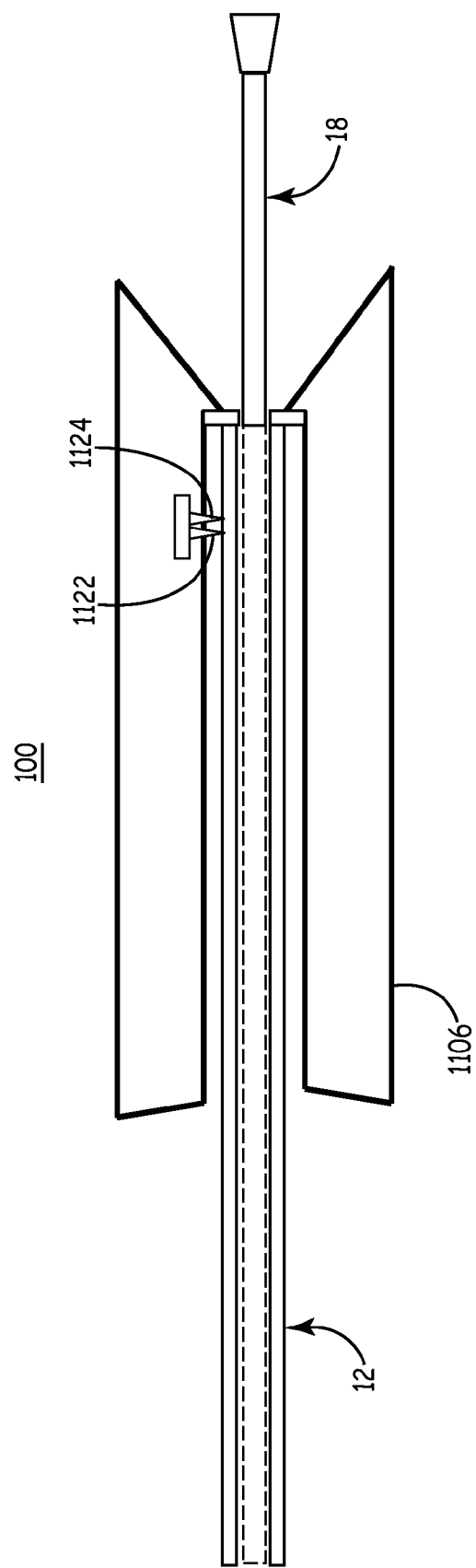
FIG. 10 is a side sectional view of the coupling device including electrical contacts.

As illustrated in FIG. 10, electrical contacts 1122, 1124 are positioned in the lead channel 1108 such that a portion of their conducting surface is exposed. The exposed portions of electrical contacts 1122, 1124 are configured to engage the electrical connector assembly (not shown) of the lead 1108. In one embodiment, the two-contact electrical arrangement electrically and mechanically couples the coupling device 1100 to lead 12 having an IS-1 standard connector assembly. In alternate embodiments of the present disclosure, additional electrical contacts may be provided on coupling device 1100 so as to correspond to any other connector assembly standard that is used for lead 12. For instance, coupling device 1100 is provided with an electrical contact arrangement that corresponds to a DF-1 connector standard, or a four contact arrangement to couple lead 12 with a connector assembly conforming to an IS-4 connector standard.

The contacts 1122, 1124 are coupled to the electrical circuitry (FIG. 11) disposed within the housing 1106. In the illustrated embodiment, the contacts 1122, 1124 are formed as spring contacts. However, the electrical contacts 1122, 1124 could take other forms such as a set screw rotated from the outer surface 1104 to engage the lead connector assembly (not shown). To facilitate electrical conduction between the lead 12 and the coupling device 1100, the electrical contacts 1122, 1124 are formed from a noble material such as platinum or gold.

Figure 11:
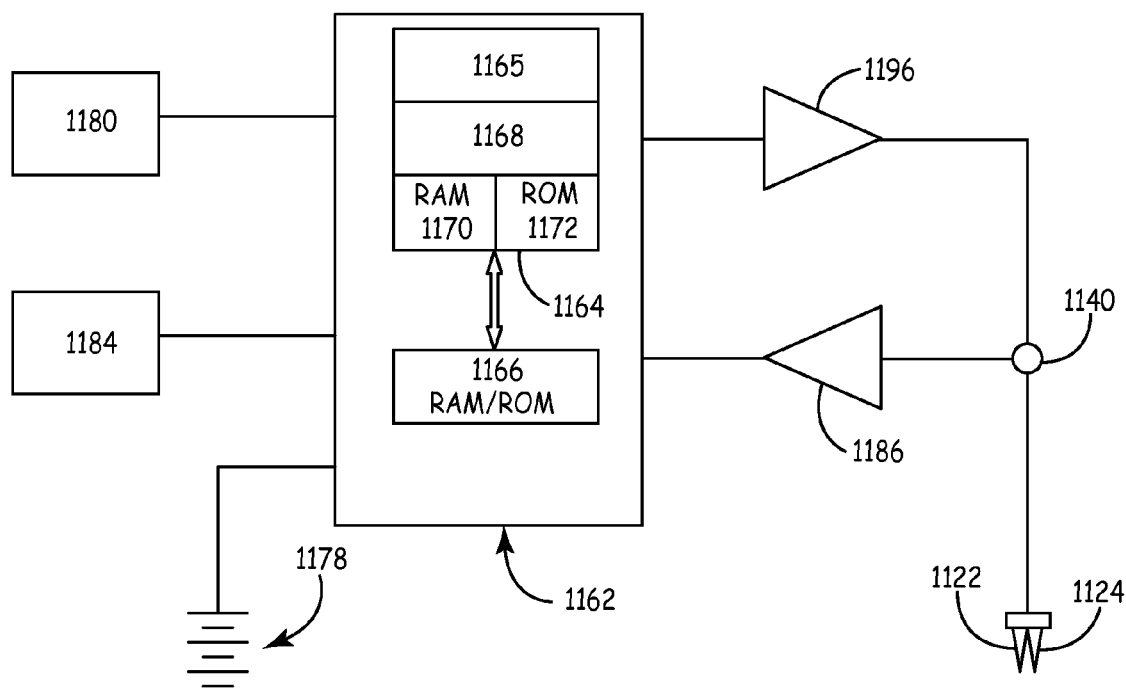
FIG. 11 is a functional block diagram illustrating various constituent electrical components of a coupling device.

FIG. 11 is a functional block diagram illustrating various electrical components of the coupling device 1100 that includes a microprocessor-based architecture. The electrical contacts 1122, 1124 are functionally coupled to a pulse generator 1196 via node 1140. Pulse generator 1196 is coupled to microcomputer circuit 1162 which is used to control and/or monitor generation of electrical energy by the pulse generator 1196 using software-implemented algorithms stored therein. Microcomputer circuit 1162 comprises on-board circuit 1164 and off-board circuit 1166. On-board circuit 1164 includes microprocessor 1165, system clock circuit 1168 and on-board RAM 1170 and ROM 1172. Off-board circuit 1166 comprises a RAM/ROM unit. A multiplexer unit 1184 is optionally coupled to microcomputer 1162 to allow selectivity of anode and cathode arrangements of the electrical connector on lead 12.

Electrical energy generated by the pulse generator 1196 is transmitted through node 1140 and this energy is provided to the lead 12 through electrical contacts 1122, 1124. In one embodiment, microcomputer circuit 1162 controls the amplitude and duration of the electrical energy generated by the pulse generator 196.

Continuing to refer to FIG. 11, sensing circuitry 1186 is coupled to the microcomputer circuit 1162 to receive one or more signals that is sensed via a sensor (not shown) or electrode (not shown) on lead 12. The sensed signals are transmitted through the lead 12 and provided to the coupling device 1100 through electrical contacts 1122, 1124. The sensed signal received at electrical contacts 1122, 1124 is transmitted through node 1140 and provided to the sensing circuitry 1186. The microcomputer circuit 1162 includes software-implemented algorithms to control the sensing operation of the coupling device 1100. The sensed signals received by the sensing circuitry 1186 include, for example, physiological signal such as impedance, voltage, current, temperature, heart rate, blood pressure, electromyography, electro-encephalography, and electro-oculography.

In additional embodiments, coupling device 1100 is configured for wireless communication with devices 130, 135 (FIGS. 1A, 1B). Therefore, a wireless communication module 1180 is coupled to the microcomputer circuit 1162 to provide the wireless communication. Devices 130, 135 are also provided with a wireless communication protocol which is compatible with the communication protocol on coupling device 1100. Any of a number of suitable programming and wireless communication protocols known in the art may be employed so long as the desired information is transmitted to and from the coupling device 1100. In alternative embodiments of the present disclosure, other communication protocols such as Bluetooth® communication, IEEE 802.11, Home RF or other short- and long-range wireless protocols may be employed as the wireless communication technique.

Any or all of the devices 105, 130 (FIG. 1A, 1B) may be used in conjunction with or as a substitute to the software implemented algorithms in microcomputer circuit 1162 to control the operation of coupling device 1100. In other words, the pulse generator 1196 provides electrical energy to lead 12 based on a command received from the microcomputer 1162 or a command transmitted by devices 105, 130. Similarly, the sensing operation by sensing circuitry 1186 may be initiated by the microcomputer 1162 or by devices 105, 130. Further, the wireless communication module 1180 provides wireless transfer of sensed data received by the coupling device 1100 to the devices 105 (via device 135), 130. It is generally preferred that the particular programming and communication protocol selected permit the entry and storage of multiple physiological parameters. However, in some embodiments of the present disclosure, the protocol chosen could be a "repeating" protocol where the sensed parameters are merely relayed to the devices 135, 130 without the need for storage.

In some embodiments, security features are incorporated into the wireless communication protocol utilized to prevent cross-talk between various devices. Exemplary embodiments of the security features of the present disclosure could include algorithms within the devices 135, 130 (FIGS. 1A, 1B) or the coupling device 1100 that initiate a communication session. The algorithms incorporate unique device identification of the coupling device 1100. Thus prior to initiating the communication session between the devices 135, 130 and the coupling device 1100, the identity of the coupling device 1100 is authenticated by devices 135, 130. Other security features known in the art may be utilized for the security function.

The electrical components shown in FIG. 11 are powered by a battery power source 1178 in accordance with common practice in the art. Such a power source could either be rechargeable or non-rechargeable.

As discussed above, implantable lead 12 varies in construction, size, and design depending on the model of the lead 12. In addition to the variations noted, some of the available leads 12 include a helical coil (not shown) at the distal tip of the lead 12. This helical coil is typically rotated into the target tissue to affix the lead 12 into the tissue. The helical coil is coupled to a conductor that extends from the distal end (not shown) to the proximal end 13 of the lead 12 and terminates at a pin 14. Subsequent to implantation of the lead 12, pin 14 is coupled to an electrical connector of a medical device (not shown) to be implanted in the patient 10. The implantation procedure of lead 12 having a helical coil therefore requires the rotation of the pin 14 which causes rotation of the helical coil in order to secure the helical coil into the target tissue.

Figure 12:
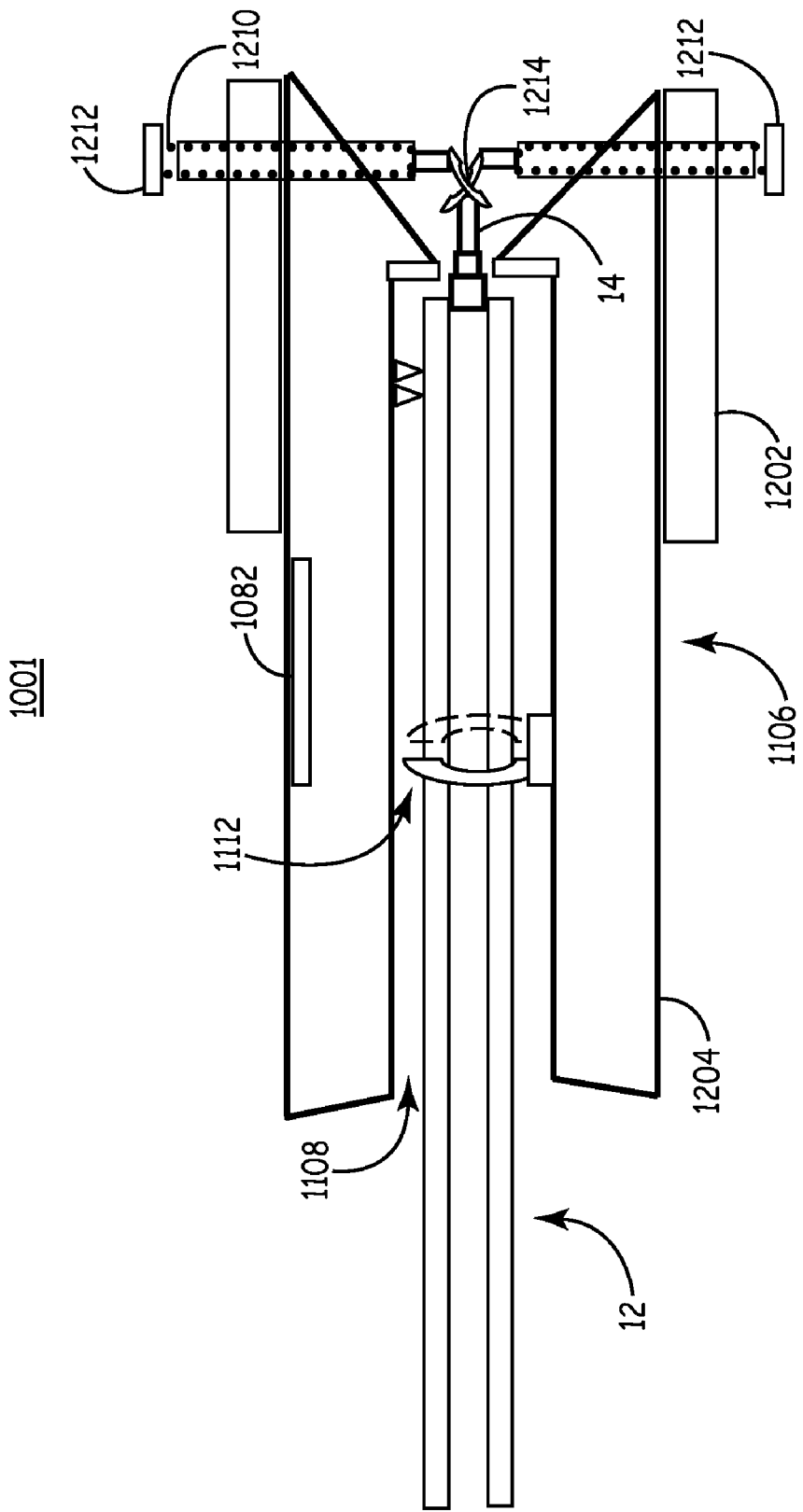
FIG. 12 depicts a side sectional view of an alternative coupling device.

Turning now to FIG. 12, an alternative embodiment of the coupling device of FIG. 9 is depicted. The coupling device 1100 includes a proximal portion 1202 and a distal portion 1204 that form a housing 1106. The proximal portion 1202 and the distal portion 1204 may be formed as an integral housing to provide a rigid coupling device 1100. In other embodiments, the proximal portion 1202 and distal portions 1204 are formed separately and interconnected to form the housing 1106. The proximal portion 1202 and distal portion 1204 are formed to permit relative rotation about one another. Housing 1106 may be formed of a plastic, metal or any other material that can be properly sterilized for use in a surgical field. Any of the fabrication processes described above with respect to FIG. 9 may be used in the fabrication of the housing 1106 illustrated in the embodiment of FIG. 12.

In the exemplary illustration of FIG. 12, engagement mechanism 1112 (described with respect to FIG. 9) is located within the distal portion 1204 of lead channel 1108 to permit gripping of a lead. This view also shows a gripping mechanism 1214 designed to grip the connector pin 14. Any gripping mechanism know in the art could be used to grip the pin 14. The exemplary mechanism 1214 is a hand actuated spring-clip 1210 that employs the use of an actuating member 1212 on the exterior surface of the proximal portion 1202. Functionally, the actuating member 1212 is compressed to expand a gripping surface of the gripping mechanism 1214 so as to position the pin 14 there-between or release the pin 14. Conversely, releasing the compressing force exerted on the actuating member 1212 causes the gripping surface to contract thereby engaging the pin 14.

The coupling devices 1100 of FIGS. 9 and 12 may optionally include a display 1082 located on an outer surface of the device 1100 to display the various aforementioned parameters that may be sensed. Displaying an indication of the sensed parameter either on the coupling device 1100 or on the devices 135, 130 is beneficial to the implanting procedure. Real time display of the sensed parameters, as the lead 12 is navigated through the patient 10 will, for example, facilitate the optimization of the implant location within the target tissue. As previously described, any of the aforementioned parameters may be sensed. In one embodiment the sensed signal is displayed as a "raw" number; in other words, the plain sensed parameter is displayed without further action. In other embodiments, the sensed parameter is processed by microcomputer 1162 to derive an indication that serves as a direct feedback to the implanting physician.

One example of a parameter that may be sensed and displayed, with or without, processing is impedance. The electrodes on lead 12 could be utilized to perform impedance measurements of the surrounding tissue or fluid as the lead 12 is progressively inserted into patient 10. The typical impedance value of blood is usually about 600 ohms while body tissue will range from about 800 ohms to over 1400 ohms. The variation of the body tissue impedance will depend on the amount of fluid in the tissue. Tissue with a normal amount of fluid is generally about 1000 ohms. Accordingly as the lead 12 is navigated through the vein (blood) into the target tissue, the impedance value will increase from about 600 ohms to 1000 ohms. This abrupt change in impedance measurement serves as an indicator to the implanting physician that lead 12 is currently in contact with tissue. The raw impedance values may be displayed and the physician may correlate the measure value with the surrounding matter e.g., plain blood, tissue with minimal fluid. Alternatively, the impedance values may be processed according to various criteria within the microprocessor 1162, and an indication of the particular matter within which the lead 12 is in contact displayed.

Additionally, the aforementioned helical coil located on lead 12 is typically rotated to secure the lead tip in the tissue. One issue that may arise with rotation of the helical coil is over-rotation that may result in damage to the tissue. It may be noted that the impedance of tissue will vary depending on the amount of fluid in the tissue. Hence, aided with display 1082 and impedance processing on microcomputer 1162 on certain embodiments of coupling device 1100, impedance measurements may be performed to facilitate the determination of when the helical coil is sufficiently rotated. As the rotation of the helical coil is performed, fluid is squeezed out of the tissue and the impedance measurement consequentially increases serving as an indication that the lead tip is successfully lodged in the tissue such that further rotation is not necessary. Moreover, because over-rotation may cause tissue damage, further rotation of the helical coil will allow blood to re-enter the fixation site and consequentially the impedance value drops. The impedance measurements performed during the rotation are displayed in real-time as the rotation occurs. Changes in impedance measurements serve as an indicator of the amount of fluid displaced from the tissue and these measurements are indicative of the portion of the helical coil that is embedded into the tissue. Thus measuring the impedance value of the tissue as the helical coil is rotated facilitates the prevention of over-rotation of the lead and thus minimizes or reduces tissue damage.

Furthermore, the coupling device 1100 may determine whether the implant location is optimal by sensing or receiving an indication of an unintended consequence. One example is phrenic nerve stimulation which may occur with a left ventricular (LV) lead since the LV lead is often implanted proximate this nerve. Either due to position or due to elevated levels for stimulation therapy, the phrenic nerve might be stimulated by the LV lead. Thus by delivering electrical energy stimulation concurrently during the implant procedure, the implanting physician may be able to identify an appropriate placement position based on the stimulation levels required for the intended therapy.

In the foregoing detailed description, the present disclosure has been described with reference to specific embodiments. However, it may be appreciated that various modifications and changes can be made without departing from the scope of the disclosure as set forth in the appended claims.

The invention claimed is:

1. A system comprising:
    a lead coupling device having a first wireless communication module, wherein the lead coupling device is adapted to receive a medical lead;
    an interface device having a second wireless communication module configured for remote communication with the first wireless module;
    a hermetically sealed medical device package;
    an implantable medical device including a connector bore and an electrical contact contained within the hermetically sealed medical device package;
    an electrical interface configured for coupling the electrical contact of the implantable medical device with the interface device, wherein the interface device is located outside the package; and
    an implantable medical device programmer, wherein the programmer is configured for communication with the implantable medical device;
    wherein the lead coupling device includes:
    a housing having a proximal opening at a proximal end and a distal opening at a distal end;
    a lead receiving channel disposed within the housing and extending from the proximal opening to the distal opening, wherein said channel is adapted to receive the medical lead;
    a pulse generator disposed within the housing for providing electrical energy;
    a processor coupled to the pulse generator;
    at least two electrical contacts mounted within the channel and coupled to the pulse generator, wherein a portion of the contacts is adapted to contact the lead; and
    a power source disposed within the housing and coupled to the pulse generator.

2. The system of claim 1, wherein the electrical interface comprises:
    a connector structure;
    a first contact surface disposed on the connector structure for electrical coupling with the electrical contact of the second device, within the connector bore of the medical device;
    a substrate;
    a second contact surface mounted on the substrate for electrical coupling with the interface device; and
    a conductive lead coupling the first contact surface to the second contact surface.

3. The system of claim 2, wherein the connector structure is adapted to allow for passage of a sterilizing gas into the bore of the connector module and past the electrical contact of the implantable medical device.

4. The system of claim 2, wherein the conductive lead of the electrical interface comprises a pin member extending distally from the first contact surface, a conductive trace extending over the substrate, and a connective interface coupling the pin member to the conductive trace.

5. The system of claim 2, wherein the electrical interface further comprises:
    a third contact surface and a fourth contact surface, each of the third and fourth contact surfaces being mounted on a side wall of the package; and
    a distal conductive lead coupling the third contact surface to the fourth contact surface and extending along the side wall of the package, wherein:
    the third contact surface is contained within the package, being directly coupled to the second contact surface; and
    the fourth contact surface is located outside the package to connect with the first medical device for electrical coupling of the first medical device to the second contact surface.

6. The system of claim 1, further comprising sensing circuitry coupled to the processor, wherein the sensing circuitry is configured to receive a physiological parameter sensed by the lead.

7. The system of claim 6, wherein the sensed physiological parameter is processed to give an indication of a medium surrounding an electrode on the lead tip.

8. The system of claim 6, wherein the wherein the sensed physiological parameter is impedance.

9. The system of claim 8, wherein the electrical interface comprises:
    a connector structure;
    a first contact surface disposed on the connector structure for electrical coupling with the electrical contact of the implantable medical device, within the bore of the medical device;
    a substrate;
    a second contact surface mounted on the substrate for electrical coupling with the interface device; and
    a conductive lead coupling the first contact surface to the second contact surface.

10. The system of claim 9, wherein the connector structure is adapted to allow for passage of a sterilizing gas into the bore and past the electrical contact of the medical device.

11. The system of claim 1, wherein the first wireless communication module includes at least one of a communication protocol comprising distance telemetry, Bluetooth, IEEE 802.11.

12. The system of claim 1, wherein the lead coupling device further includes a display.

13. The system of claim 1, wherein the proximal end and the distal end are rotatably coupled so that relative rotation is permitted between the proximal end and the distal end.

* * * * *